United States Patent [19]
Sugiyama

[11] 4,428,235
[45] Jan. 31, 1984

[54] NON-DESTRUCTIVE INSPECTION BY FREQUENCY SPECTRUM RESOLUTION

[75] Inventor: Sakae Sugiyama, Ibaraki, Japan

[73] Assignee: Hitachi, Ltd., Tokyo, Japan

[21] Appl. No.: 274,428

[22] Filed: Jun. 17, 1981

[30] Foreign Application Priority Data

Jun. 20, 1980 [JP] Japan .................................. 55-84215
Aug. 20, 1980 [JP] Japan ................................ 55-115120

[51] Int. Cl.³ .......................................... G01N 29/04
[52] U.S. Cl. ...................................... 73/579; 73/582; 73/602
[58] Field of Search ................. 73/579, 582, 602, 588, 73/629

[56] References Cited

U.S. PATENT DOCUMENTS 3,332,278 7/1967 Wood et al. .......................... 73/602
3,538,753 11/1970 Gericke ................................ 73/602
3,756,071 9/1973 Dory ..................................... 73/602
3,776,026 12/1973 Adler et al. .......................... 73/602
4,228,804 10/1980 Holaser et al. ...................... 73/602

Primary Examiner—Anthony V. Ciartante
Attorney, Agent, or Firm—Thomas E. Beall, Jr.

[57] ABSTRACT

A method of inspecting non-destructively a specimen for examining the presence or absence of a defect in the specimen, in which an ultrasonic wave is emitted from a probe and a reflected wave from the specimen is received by the probe whose output signal is processed to determine the presence or absence of the defect. The signal processing includes steps of extracting characteristic parameters from a frequency spectrum of the ultrasonic echo and comparing the extracted parameter with corresponding experimentally or theoretically determined values. The invention makes it possible to automatically determine discriminatively whether the reflector of the ultrasonic echo is a configured portion, a weld boundary or a defect of a specimen to be inspected.

9 Claims, 11 Drawing Figures

NON-DESTRUCTIVE INSPECTION BY FREQUENCY SPECTRUM RESOLUTION

BACKGROUND OF THE INVENTION

The present invention relates to a non-destructive inspecting method suited for determining the nature or character and size of a reflector of an ultrasonic echo and an apparatus for carrying out the method.

As a method for inspecting a specimen of a metallic material as to the presence of defects such as the one present in the interior of the metal material, fusion failure in a welded portion, slag inclusion and the like, there has been known a method of determining information about these defects on the basis of a frequency spectrum derived through frequency resolution of ultrasonic echoes reflected from the defects. A typical one of such methods is disclosed in U.S. Pat. No. 3,776,026 titled "ULTRASONIC FLAW-DETERMINATION BY SPECTRAL ANALYSIS". According to this method, the size d of a defect is determined on the basis of a frequency spacing $\Delta f$ between maxima in the frequency spectrum in accordance with the following expression (1):

$$d = c/\Delta f \cdot \sin \theta \qquad (1)$$

where c represents speed of sound (mm/s) of an ultrasonic wave, $\theta$ represents an incident angle, $\Delta f$ represents the frequency spacing (Hz) between maxima in the frequency spectrum, and d represents the size of a defect.

SUMMARY OF THE INVENTION

However, in practical applications, there arises such a case in which the frequency spacing $\Delta f$ can not be determined because of a single-peak pattern of the ultrasonic echo reflected from a certain type of reflector. Further, the frequency spacing $\Delta f$ making appearance in the frequency spectrum does not necessarily mean that an ideal pattern is available, unless the peaks appear at a constant spacing. Meanwhile, besides the determination of the size of a defect, it is also very important from the standpoint of the quality control of structures to detect non-destructively the nature or character of the defect, i.e. whether the reflector is a weld boundary or really a crack or a fusion failure. Taking these problems into consideration, the hitherto known method capable of determining the size of a defect at the constant frequency spacing in the frequency spectrum of the echo signal is still disadvantageous in that the range to which the method can be applied is restricted.

An object of the present invention is to provide a non-destructive inspecting method which is capable of automatically determining discriminatively whether a reflector of a received echo is a configured or profiled portion of a specimen to be inspected, a weld boundary or a defect and additionally estimating the size of defect if it is present.

Another object of the invention is to provide an apparatus for carrying out the method described above.

According to an aspect of the invention, characteristic parameters are extracted from a frequency spectrum of an ultrasonic echo and subsequently compared with respective values which have previously been determined experimentally or theoretically, thereby to identify the nature or character of the reflector and determine the size of a defect when detected.

Typical patterns of ultrasonic echoes include (a) a pattern of a single peak, (b) a pattern of multiple peaks of a constant pitch and (c) a pattern of multiple peaks of a variable pitch. It has experimentally been confirmed that the frequency spectrum patterns described above interchange with one another in dependence on whether the reflector of the ultrasonic wave is a geometrical or configurational boundary of the specimen to be inspected, a defect in the specimen or a weld boundary. Accordingly, it is possible to discriminatively determine whether the ultrasonic echo is ascribable to the defect, the weld boundary or an inherent geometrical factor of a specimen by detecting the differences among the frequency spectrum patterns.

According to a feature of the invention, the relationship between or among characteristic parameters derived from the ultrasonic echo is made use of for discriminatively identifying the different frequency spectrum patterns. More particularly, it is previously determined experimentally or theoretically in what manner the characteristic parameters of the ultrasonic echo vary in dependence on the natures or characters of the reflector, whereby the experimentally or theoretically determined values, that is reference values, are compared with the corresponding measured values.

BRIEF DESCRIPTION OF THE DRAWING

These and other objects and advantages of the invention will become more apparent upon a reading of the following description in which the preferred embodiment has been set forth in detail in conjunction with the accompanying drawings, in which.

DETAILED DESCRIPTION

A first exemplary embodiment of the present invention will be described in detail by referring to FIGS. 1a to 1c and FIG. 2.

Figure 1A:
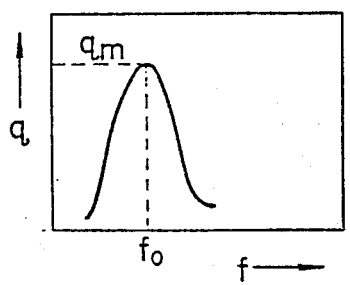
FIGS. 1a to 1c graphically illustrate typical patterns of frequency spectra of ultrasonic echoes.
Figure 1B:
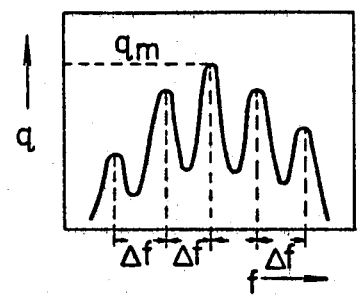
Figure 1C:
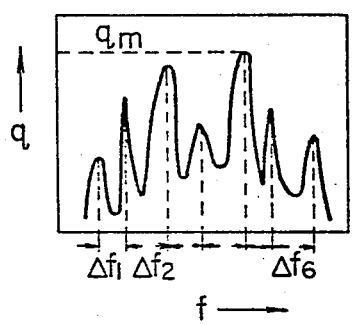

In FIGS. 1a, 1b and 1c, there are graphically illustrated, respectively, a single peak pattern, a pattern of multiple peaks of a constant pitch and a pattern of multiple peaks of a variable pitch, as mentioned hereinbefore. In these graphs, frequency f is taken along the abscissa, while a spectrum strength q is taken along the ordinate. In the case of the first exemplary embodiment being now described, the following four parameters are employed as the characteristic parameters mentioned hereinbefore. Namely,
(1) maximum spectrum strength ($q_m$),
(2) center frequency ($f_o$),
(3) mean value of frequency spacing between maxima in a frequency spectrum ($\overline{\Delta f}$), and
(4) standard deviation of the frequency spacing between maxima in the frequency spectrum ($\sigma_f$).

Figure 2:
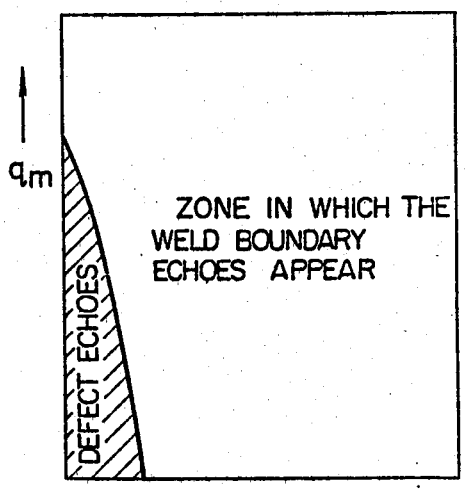
FIG. 2 shows a map used for discriminating echoes from a weld boundary and a defect.

FIG. 2 illustrates a principle of a method of discriminating a weld boundary and a defect from each other. It has experimentally been established that an ultrasonic echo from the defect tends to present the single peak pattern (FIG. 1a) or the pattern of multiple peaks of a constant pitch. In contrast, the ultrasonic echo from the weld boundary has numerous echoes superposed thereon, which are reflected from the boundary with minute differences in time. Accordingly, the frequency spectrum of the echo from the weld boundary has a great standard deviation $\sigma_f$ of the frequency spacing between the maxima as well as the maximum spectrum strength $q_m$ of a great magnitude. In this connection, it should be noted that determination of the frequency spectrum be executed after the amplitudes of the ultrasonic echo taken as a function of time have been regulated to a constant level. The echo from an inherent geometrical or configurational boundary of a specimen to be examined tends to take the single peak pattern, because the echo from the geometrical or configurational boundary is brought about by a single reflection. In the case of the echo having the pattern of a single peak, there is available no frequency spacing parameter $\overline{\Delta f}$. For convenience's sake, it is however assumed that the standard deviation $\sigma_f$ of the frequency spacing is zero.

The center frequency $f_o$ and the mean frequency spacing $\overline{\Delta f}$ (i.e. the mean value of the frequency spacings) are primarily made use of for estimating a size of a reflector. In the case where the size d of a defect is to be estimated in accordance with the aforementioned expression (1) disclosed in U.S. Pat. No. 3,776,026, the frequency spacing $\Delta f$ has heretofore been employed. In contrast, the invention teaches the use of the mean frequency spacing $\overline{\Delta f}$ in consideration of the fact that the frequency spacing $\Delta f$ is rarely uniform or constant in the pattern of multiple peaks. On the other hand, the center frequency $f_o$ tends to be increased, as the size d of the reflector becomes smaller. For a quantitative analysis, the center frequency $f_o$ is previously determined through experimental measurement made on a specimen of a known material having a defect of a known size. The center frequency $f_o$ thus predetermined for the known specimen is utilized for determining the center frequency $f_o$ of an unknown specimen through comparison with the results of measurement made on the latter.

Figure 3:
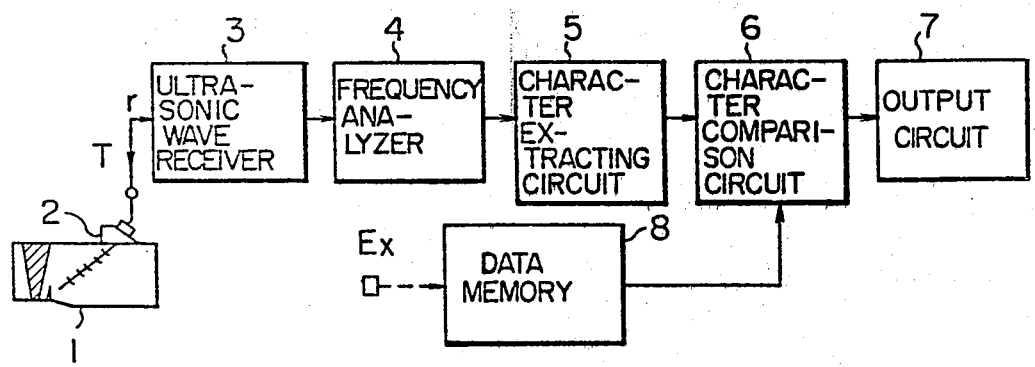
FIG. 3 is a view to show a general arrangement of an apparatus according to an exemplary embodiment of the invention.

FIG. 3 shows a second exemplary embodiment of the present invention and illustrates an example of the apparatus for carrying out the non-destructive inspecting method described above in conjunction with the first exemplary embodiment of the invention.

The apparatus shown in FIG. 3 is so arranged as to identify characteristic features (i.e. inherent geometrical or configurational boundary, weld boundary and/or defect) of a reflector f present in a specimen 1 to be inspected and determine the size of a defect, if it is present. To this end, the apparatus includes a probe 2 and an ultrasonic receiver 3 which are usually employed in conventional ultrasonic defect inspections and additionally includes a frequency analyzer circuit 4, a character extracting circuit 5, a character comparing circuit 6, an output circuit 7 and a data storage circuit 8.

The frequency analyzer circuit 4 is adapted to calculate the spectrum strength q on the basis of a predetermined time duration $\tau$ of a radio frequency (RF) signal of an ultrasonic echo R in accordance with the following expression:

$$q(f) = \left| \int_{-\tau/2}^{\tau/2} r(t)e^{-j\omega t} dt \right| \quad (2)$$

where r(t) is a function representative of the ultrasonic echo R, f represents its frequency, and $\omega = 2\pi f$.

Figure 4:
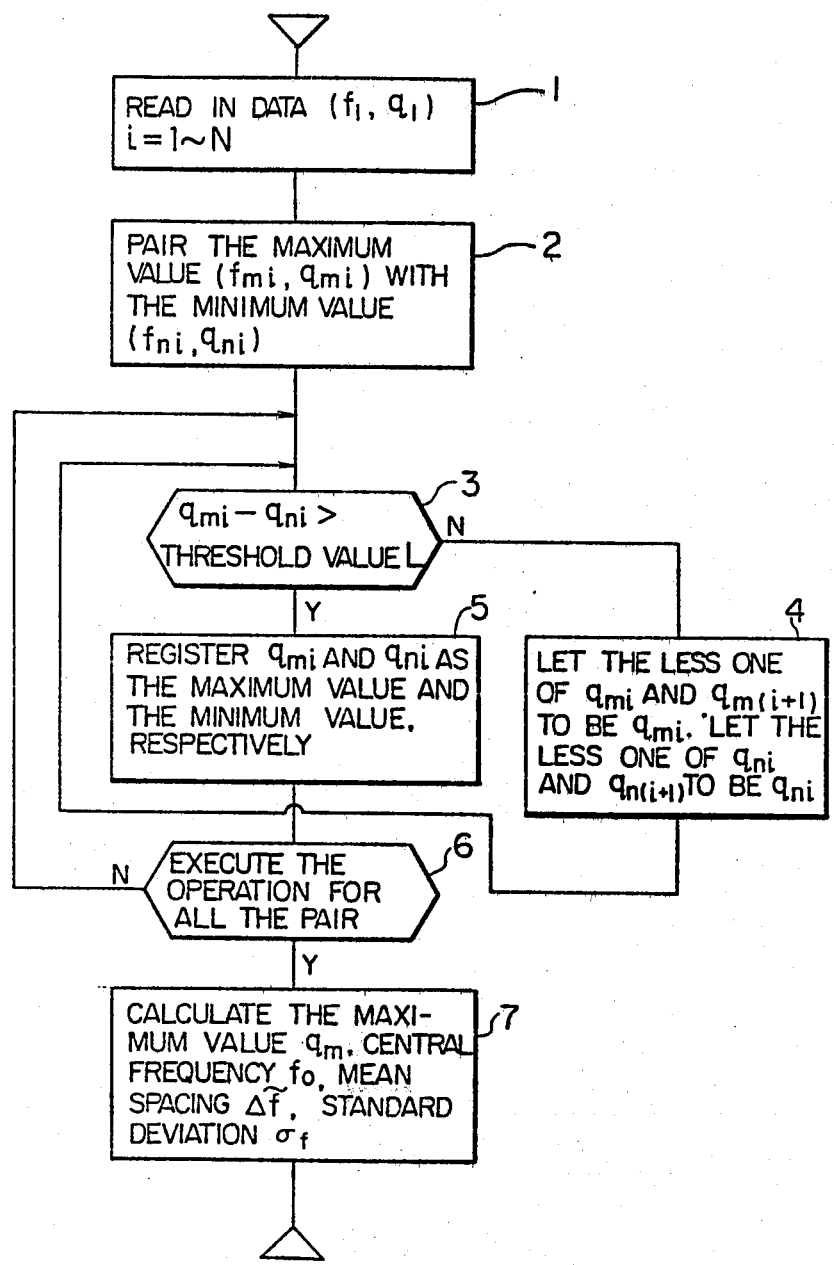
FIGS. 4 and 5 illustrate in respective flow charts operations of a character extracting circuit and a character comparing circuit which constitute parts of the apparatus according to the invention.

The character extracting circuit 5 serves to extract the four characteristic parameters described hereinbefore. More particularly, the character extracting circuit 5 receives input data $f_i$ and $q_i$ (where i = 1 to N) from the frequency analyzer circuit 4 and arithmetically determines the parameters $q_m$, $f_o$, $\overline{\Delta f}$ and $\sigma_f$ defined hereinbefore in accordance with the procedure illustrated in a flow chart of FIG. 4. At steps 3, 4 and 5 of this procedure, those variations (pulsations) which are smaller than a predetermined threshold value L are smoothed.

Figure 5:
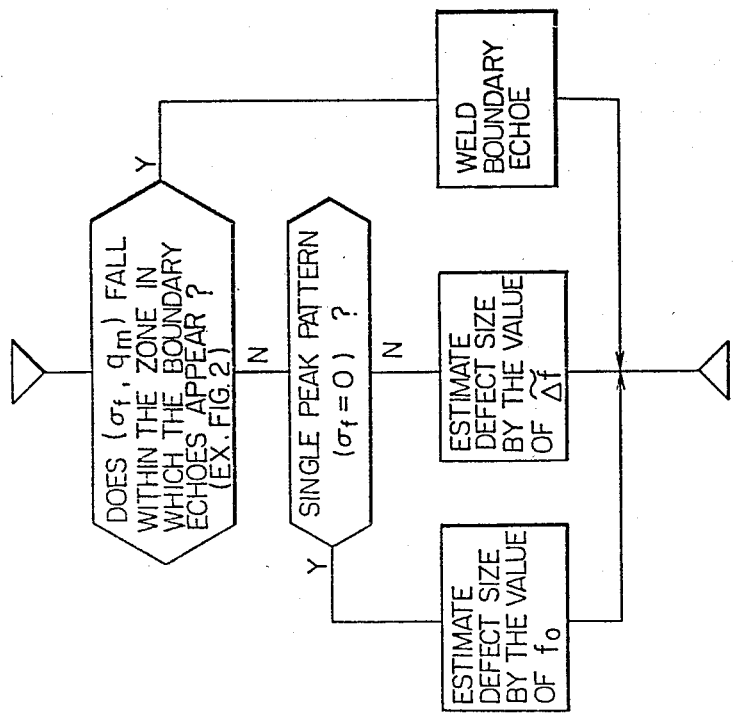

In the character comparing circuit 6, the fresh characteristic parameters thus obtained by the ultrasonic defect inspections are compared with the associated data stored in the data storage circuit 8, thereby to identify the characters of the reflector of the ultrasonic echo r(t) and estimate the size of a defect, if present. To this end, a map illustrated in FIG. 2 may be stored in the data storage circuit 8. Further, relationships between the size d of defect and the center frequency $f_o$ are listed in a table in combination with materials of specimen to be inspected and shapes of defect (e.g. shapes of circle, slit and the like). This table is also stored in the data storage circuit 8. These informations or data are exteriorly supplied as input data Ex. With the circuit arrangement mentioned above, a procedure for estimating the size of a defect may be implemented in such a manner as illustrated in FIG. 5.

Figure 6:
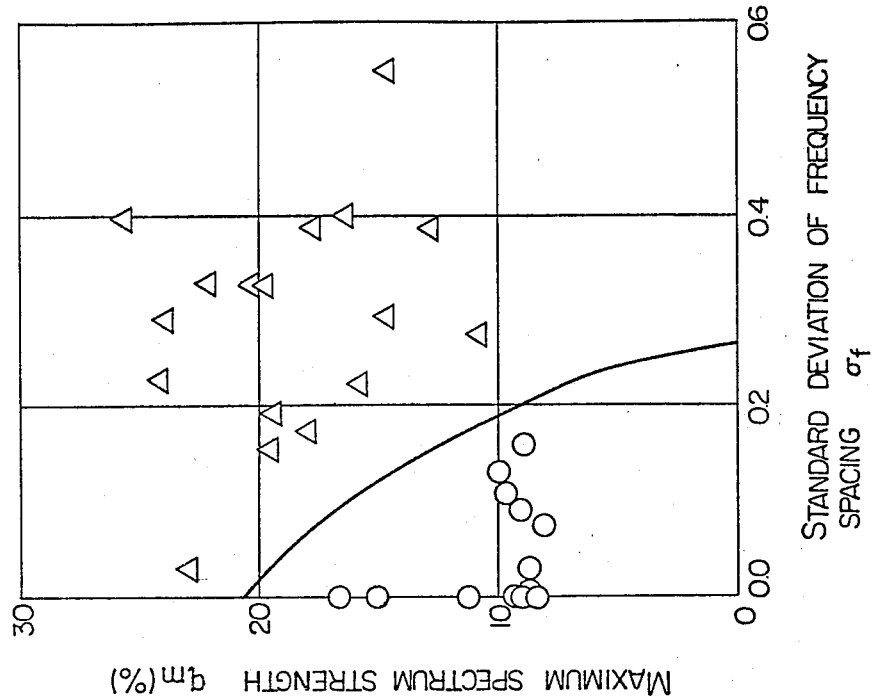
FIG. 6 illustrates results of experiments conducted according to the teaching of the invention.

The output circuit 7 may be constituted by a X-Y plotter or a cathode ray tube (CRT) and serves for displaying the parameter data $q_m$ and $\sigma_f$ of the measured ultrasonic echo on a map such as one shown in FIG. 2. FIG. 6 graphically illustrates results of experiments conducted for the weld boundary and various defects (slit-like defects, drilled bores, natural cracks or the like) of a welded portion of different type metals.

In the foregoing, the spectrum strength q is calculated on the basis of the expression (2). However, in order to obviate the influence exerted by the probe, the spectrum strength q may be determined according to the following expression:

$$q(f) = \frac{1}{q_p(f)} \left| \int_{-\tau/2}^{\tau/2} r(t)e^{-j\omega t} dt \right| \quad (3)$$

where $q_p(f)$ represents the frequency spectrum of the probe.

Next, a third exemplary embodiment of the invention will be described in detail by referring to FIGS. 7 and 8.

According to this embodiment, an inner worked portion and a defect of a specimen are discriminated from each other by using the characteristic parameters in the frequency spectrum of the ultrasonic echo.

Figure 7:
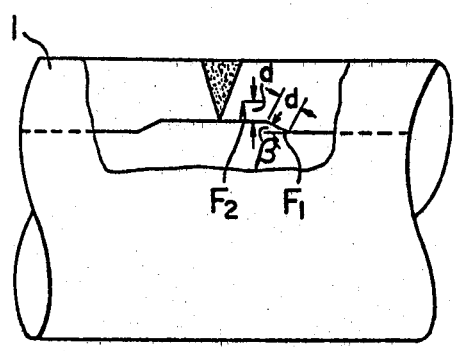
FIG. 7 schematically illustrates an example of specimen to be inspected.
Figure 8A:
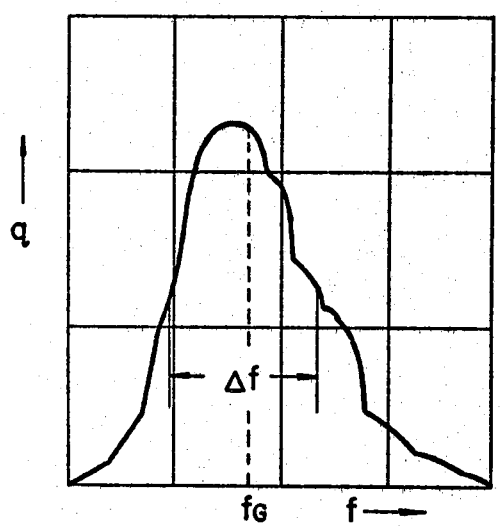
FIGS. 8a and 8b show typical examples of frequency spectrum patterns.
Figure 8B:
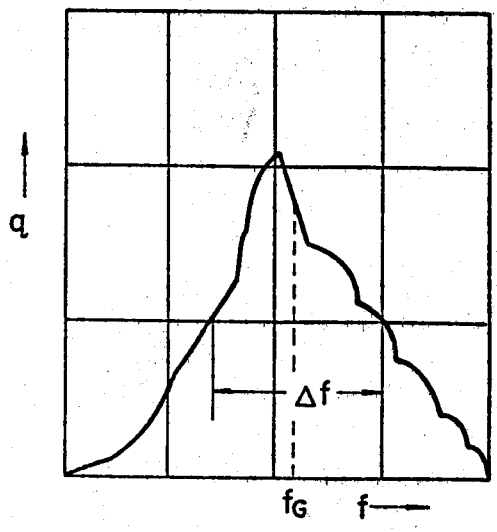

FIG. 7 shows schematically the specimen to be inspected. In this figure, a reference letter d represents the length of an inner worked portion $F_1$ or the depth of a crack $F_2$, and $\beta$ represents an inclination angle of the inner worked portion. In the case of an ultrasonic defect inspection of a welded portion of conduits, ultrasonic echoes are produced from the inner worked portion $F_1$ and the defect (crack) $F_2$. Since the difference can not be recognized between these ultrasonic echoes by means of an A-scope, discrimination is made with the aid of the frequency spectrum patterns. FIGS. 8a and 8b graphically illustrate typical examples of frequency spectra q of the ultrasonic echoes produced from the crack $F_2$ and the inner worked portion $F_1$, respectively. From the results of numerous experiments made on specimens of which the inclination angle $\beta$ and the length d are varied within a range of normal values as well as the specimens of which the crack depth d is varied in a range of several millimeters, it has been found that differences in the frequency spectrum between the inner worked portion and the cracks can be defined as follows:

(1) The frequency spectrum pattern associated with a crack is characterized in that either a bary-center frequency $f_G$ is low or the frequency spacing $\Delta f$ is narrow (FIG. 8a).

(2) The frequency spectrum pattern associated with an inner worked portion is characterized in that either the bary-center frequency $f_G$ is high or the frequency spacing $\Delta f$ is wide (FIG. 8b) in opposition to the frequency spectrum pattern ascribable to the crack.

On the basis of the characteristics described above, it is possible to discriminate the crack from the inner worked portion. For quantitative analysis, the bary-center frequency $f_G$ as well as the frequency width $\Delta f$ of a reference or control specimen made of a predetermined material and formed with a known inner worked portion and a known crack are previously determined and compared with those of specimens to be inspected which is made of a same material as that of the reference specimen and whose reflector is unknown, whereby the nature or the character of the reflector can be determined on the basis of the result of the comparison.

Figure 9:
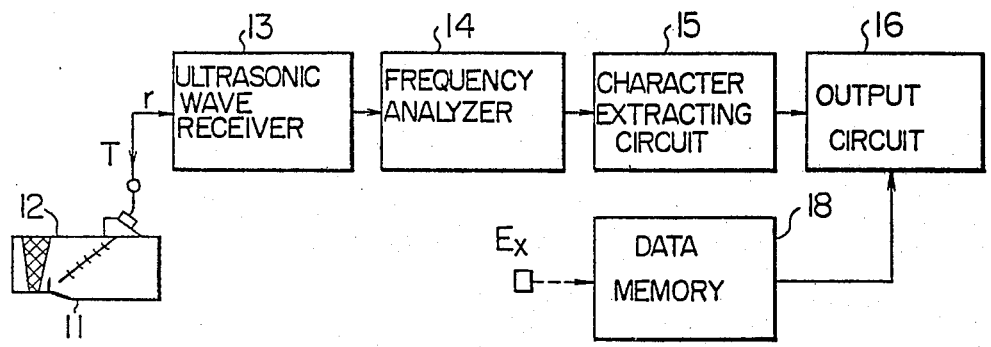
FIG. 9 shows in a block diagram a general arrangement of the apparatus according to an embodiment of the invention.
Figure 10:
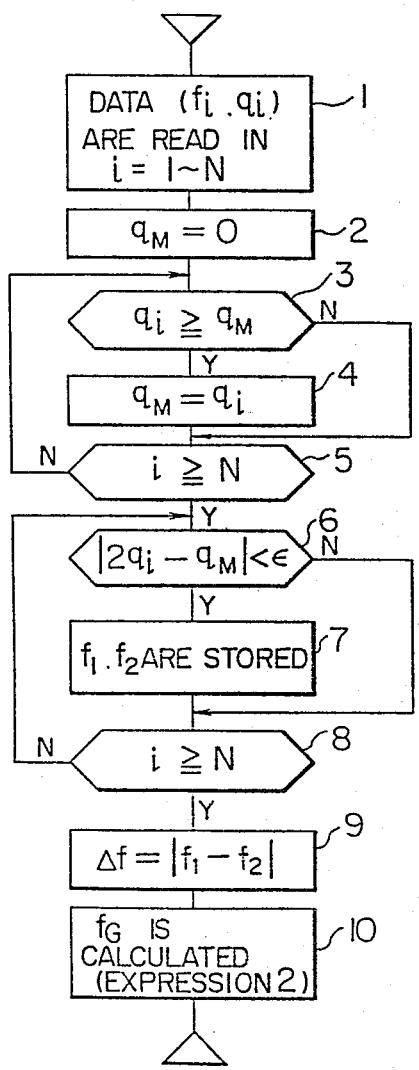
FIG. 10 shows a flow chart to illustrate a procedure for extracting characteristic parameters.
Figure 11:
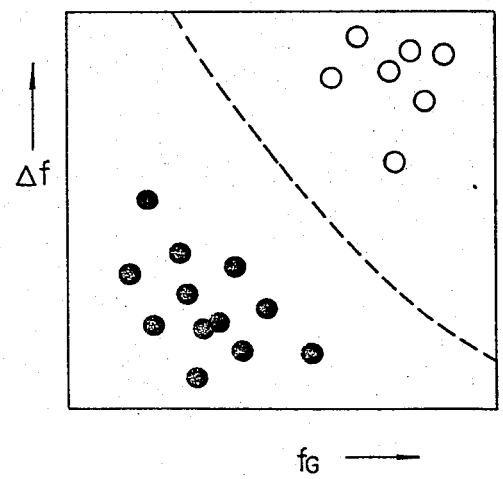
FIG. 11 shows a two-dimensional map used for discriminatively identifying reflectors.

Next, a fourth exemplary embodiment of the present invention will be described by referring to FIGS. 9 to 11. The fourth embodiment concerns an apparatus for carrying out the method according to the third exemplary embodiment of the invention. The apparatus comprises, in addition to a probe 12 and an ultrasonic receiver 13 employed in conventional ultrasonic defect inspection, a frequency analyzer circuit 14 for identifying characters or natures of reflectors $F_1$ and $F_2$ possibly present in a specimen to be inspected, a character extracting circuit 15, an output circuit 16 and a data storage circuit 18.

The frequency analyzer circuit 14 is adapted to calculate the spectrum intensity or strength q(f) on the basis of a predetermined time duration $\tau$ of a radio frequency (RF) signal representative of the ultrasonic echo r(t) in accordance with the following expression:

$$q(f) = \left| \int_{-\tau/2}^{\tau/2} r(t)e^{-j\omega t} dt \right| \quad (4)$$

where r(t) represents the ultrasonic echo, f represents the frequency of the echo signal, and $\omega = 2\pi f$.

The character extracting circuit serves to extract the two characteristic parameters, i.e. the bary-center frequency $f_G$ and the frequency spacing $\Delta f$ from the measured frequency spectrum. More specifically, the character extracting circuit 15 receives at the input thereof the data $f_i$ and $q_i$ (where I=1 to N) from the frequency analyzer circuit 14 and arithmetically determine the bary-center frequency $f_G$ and the frequency spacing $\Delta f$ in accordance with the procedure executed at steps 1 to 9 illustrated in a flow chart of FIG. 10 in which $q_m$ represents the maximum spectrum strength, and $\epsilon$ represents a tolerable deviation in the selection of a half-strength level.

The bary-center frequency $f_G$ can be calculated in accordance with the following expression (5):

$$f_G = \frac{\sum_{i=1}^{N} f_i q_i}{\sum_{i=1}^{N} q_i} \quad (5)$$

The output circuit 16 serves to depict on a two-dimensional map the bary-center frequency $f_G$ and the frequency spacing $\Delta f$ in the frequency spectrum of the ultrasonic echo from a certain reflector F and may be constituted by a cathode ray tube, an X-Y plotter or the like in practical applications. FIG. 11 illustrates an example of the two-dimensional map which can be conveniently employed for discriminating an inner worked portion and a crack. In the figure, hollow circles correspond to the inner worked portion, while the solid circles correspond to the crack. The boundary (indicated by a broken line) between the hollow circle area and the solid circle area is determined on the basis of the result of experiment conducted by using a known specimen. The boundary line is stored in the data storage circuit 18 as one of the input data Ex and supplied to the output circuit 16.

Although the foregoing description has been made on the assumption that the non-destructive inspecting apparatus is composed of specific devices, it will be appreciated that the invention may be carried out with the aid of a microcomputer or the like. In the latter case, the signal output from the receiver is subjected to an analog-to-digital conversion and then undergoes the frequency analysis, the character extraction and the character comparison by means of the microcomputer. Alternatively, only the character extraction and the character comparison may be executed by the microcomputer.

What is claimed is:

1. In a method of inspecting non-destructively a specimen for examining the presence or absence of a defect in said specimen, in which an ultrasonic wave is emitted from a probe and a reflected wave from said specimen is received by said probe whose output signal is processed to determine the presence or absence of said defect, said processing comprising:

deriving a frequency spectrum signal representative of the freuency spectrum of said output signal;

deriving at least two separate characteristic parameter signals of the frequency spectrum from said frequency spectrum signal, said characteristic parameters including a maximum spectrum density and a standard deviation of frequency spacing between maxima in the frequency spectrum of said frequency spectrum signal;

comparing said characteristic parameter signals with reference signals representative of predetermined corresponding characteristic parameters of maximum spectrum density and a standard deviation of frequency spacing between maxima in the frequency spectrum for both a defect and a boundary in a similar reference material; and discriminating between a defect and a boundary based upon said step of comparing.

2. A non-destructive inspecting method according to claim 1, wherein said step of deriving includes characteristic parameters of bary-center frequency and a frequency spacing between maxima of said frequency spectrum; said step of comparing further includes reference signals of bary-center frequency and frequency spacing between maxima of said frequency spectrum for both a defect and an inner working in a similar reference material; and said step of discriminating discriminates between a defect and an inner working based upon said step of comparing.

3. In a method of inspecting non-destructively a specimen for examining the presence or absence of a defect in said specimen, in which an ultrasonic wave is emitted from a probe and a reflected wave from said specimen is received by said probe whose output signal is processed to determine the presence or absence of said defect, said processing comprising:

arithmetically determining a frequency spectrum of said probe output signal to thereby extract two parameters of a bary-center frequency ($f_G$) and a frequency spacing ($\Delta f$) between maxima of said frequency spectrum;

plotting said two parameters ($f_G$, $\Delta f$) on a reference two-dimensional map having one axis along which one of said parameters is taken, said reference two-dimensional map including a plurality of reference points of said parameters for similar references sufficient in variety and quantity to establish a boundary line between a defect and a non-defect; and based upon said plotting, determining discriminatively whether the reflector portion of the specimen is an inner worked non-defect portion or a crack defect present in said specimen by referring to said boundary line between the inner worked portion and the defect crack on said plot.

4. A method of inspecting non-destructively a specimen for examining the presence or absence of a defect in said specimen, in which an ultrasonic wave is emitted from a probe and a reflected wave from said specimen is received by said probe, whose output signal is processed to determine the presence or absence of said defect, said processing comprising:

deriving a frequency spectrum signal representative of the frequency spectrum of said output signal;

deriving at least two separate characteristic parameter signals of the frequency spectrum from said frequency spectrum signal, said characteristic parameters including a bary-center frequency and a frequency spacing between maxima of said frequency spectrum of said frequency spectrum signal;

comparing said characteristic parameter signals with reference signals representative of predetermined corresponding characteristic parameters of bary-center frequency and frequency spacing between maxima of said frequency spectrum for both an inner working and a defect in a similar reference material; and discriminating between a defect and an inner working based upon said step of comparing.

5. Apparatus for inspecting non-destructively a specimen for examining the presence or absence of a defect in said specimen, comprising:

means for emitting an ultrasonic wave from a probe to the specimen, for receiving with said probe a reflected wave of said ultrasonic wave from said specimen, and producing an output signal corresponding to the received reflected wave;

means deriving a frequency spectrum signal representative of the frequency spectrum of said output signal;

means deriving at least two separate characteristic parameter signals of the frequency spectrum from said frequency spectrum signal, said characteristic parameters including a maximum spectrum density and a standard deviation of frequency spacing between maxima of the frequency spectrum of said frequency spectrum signal;

means comparing said characteristic parameter signals with reference signals representative of predetermined corresponding characteristic parameters of maxima spectrum density and a standard deviation of frequency spacing between maxima in the frequency spectrum for both a defect and a boundary in a similar reference material; and means discriminating between a defect and a boundary based upon the comparing provided by said means for comparing.

6. The apparatus according to claim 5, further including means storing said reference signals as a two-dimensional map having one axis along which one of said parameters is taken and the other axis along which the other of said parameters is taken, with said reference signals being sufficient in quantity and variety to provide a boundary line between reference signals corresponding to a defect and reference signals corresponding to a boundary.

7. Apparatus for inspecting non-destructively a specimen for examining the presence or absence of a defect in said specimen, comprising:

means for emitting an ultrasonic wave from a probe to the specimen, for receiving with said probe a reflected wave of said ultrasonic wave from said specimen, and producing an output signal corresponding to the received reflected wave;

means deriving a frequency spectrum signal representative of the frequency spectrum of said output signal;

means deriving at least two separate characteristic parameter signals of the frequency spectrum from said frequency spectrum signal, said characteristic parameters including a bary-center frequency and a frequency spacing between maxima of the frequency spectrum of said frequency spectrum signal;

means comparing said characteristic parameter signals with reference signals representative of predetermined corresponding characteristic parameters of bary-center frequency and frequency spacing between maxima of said frequency spectrum for both an inner working and a defect in a similar reference material; and means discriminating between a defect and an inner working based upon the comparing provided by said means for comparing.

8. The apparatus according to claim 7, further including means storing said reference signals as a two-dimensional map having one axis along which one of said parameters is taken and the other axis along which the other of said parameters is taken, with said reference signals being sufficient in quantity and variety to provide a boundary line between reference signals corresponding to a defect and reference signals corresponding to an inner working area.

9. In a method of inspecting non-destructively a specimen for examining the presence or absence of a defect in said specimen, in which an ultrasonic wave is emitted from a probe and a reflected wave from said specimen is received by said probe whose output signal is processed to determine the presence or absence of said defect, said processing comprising:

arithmetically determining a frequency spectrum of said probe output signal to thereby extract two parameters of a maximum spectrum density and a mean value of frequency spacing between maxima of said frequency spectrum;

plotting said two parameters on a reference two-dimensional map having one axis along which one of said parameters is taken and the other axis along which the other of said parameters is taken; and based upon said plotting determining discriminatively whether the reflector portion of the specimen is a boundary non-defect portion or a defect present in said specimen by referring to said boundary line between the boundary portion and the defect on said plot.

* * * * *